(12) United States Patent
Parker

(10) Patent No.: US 7,236,813 B2
(45) Date of Patent: Jun. 26, 2007

(54) OPTICAL DEVICE

(75) Inventor: Dawood Parker, Dyfed (GB)

(73) Assignee: Edwards Lifesciences Corporation, Irvine, CA (US)

( * ) Notice: Subject to any disclaimer, the term of this patent is extended or adjusted under 35 U.S.C. 154(b) by 173 days.

(21) Appl. No.: 10/994,682

(22) Filed: Nov. 22, 2004

(65) Prior Publication Data

US 2005/0101850 A1   May 12, 2005

Related U.S. Application Data

(62) Division of application No. 09/762,923, filed as application No. PCT/GB99/02510 on Jul. 30, 1999, now Pat. No. 6,842,635.

(30) Foreign Application Priority Data

Aug. 13, 1998  (GB) .................................. 9817552.4
Feb. 25, 1999  (GB) .................................. 9904232.7

(51) Int. Cl.
*A61B 5/00* (2006.01)
(52) U.S. Cl. ...................................... 600/323; 600/336
(58) Field of Classification Search ................ 600/322, 600/323, 331, 338, 336
See application file for complete search history.

(56) References Cited

U.S. PATENT DOCUMENTS 3,638,640 A   2/1972  Shaw
4,273,442 A   6/1981  Lübbers
5,413,100 A   5/1995  Barthelemy et al.
5,575,285 A   11/1996 Takanashi et al.
5,672,875 A   9/1997  Block et al.

FOREIGN PATENT DOCUMENTS

| DE | 33 28 862 A1 |   | 2/1985 |
|----|-------------|---|--------|
| EP | 0286142 |   | 10/1988 |
| EP | 0374844 |   | 6/1990 |
| EP | 0548027 A2 |   | 6/1993 |
| EP | 0586025 A2 |   | 3/1994 |
| WO | WO 91/01678 |   | 2/1991 |
| WO | WO 92/21283 | * | 12/1992 |
| WO | WO 94/03102 |   | 2/1994 |
| WO | WO 00/09004 |   | 2/2000 |

* cited by examiner

*Primary Examiner*—Eric Winkaur
*Assistant Examiner*—Etsub Berhanu
(74) *Attorney, Agent, or Firm*—Gregory J. Carlin; Edwin D. Schindler; Rajiv Yadav

(57) ABSTRACT

A method for monitoring blood oxygen saturation ($SO_2$) includes the steps of calculating an estimate of $SO_2$ in the blood and correcting the estimate by a scaling factor. A preferred embodiment of the method includes the steps of transmitting light containing a plurality of wavelengths into the blood; measuring a remitted spectrum over the plurality of wavelengths; calculating a measured blood absorption spectrum from the remitted spectrum; estimating local rates of change in the measured blood absorption spectrum at a plurality of the wavelengths; and calculating the estimate of $SO_2$ as a function of absolute values of the local rates of change of the measured blood absorption spectrum.

4 Claims, 9 Drawing Sheets

OPTICAL DEVICE

CROSS-REFERENCE TO RELATED APPLICATION

This is a division of application Ser. No. 09/762,923, filed Apr. 16, 2001 now U.S. Pat. No. 6,812,635, which represents the U.S. National Phase, pursuant to 35 U.S.C. §371, of P.C.T. Application No. PCT/GB99/02510, filed Jul. 30, 1999.

BACKGROUND OF THE INVENTION

1. Technical Field of the Invention

This invention relates to an optical device for monitoring or measuring/displaying the arterial oxygen saturation with motion artefact suppression and to a novel medical technique for providing arterial oxygen saturation data.

2. Description of the Prior Art

Monitors are available which use non-invasive optical techniques to measure the arterial oxygen saturation in patients. For example, it is known, that in order to measure blood oxygen saturation, it is necessary to provide a device which passes light through biological tissue, such as the human finger, and to monitor the transmitted or reflected output signal from a photodetector of this device continuously. Such devices are described, inter alia, in International Patent Application No. WO94/03102.

As is well known in the art, these instruments suffer interference due to patient movement, i.e. motion artefact.

Movement of the subject leads to a change in the length of the path of the light through the biological tissue and hence to a variation in the intensity of light received by the photodetector. This renders the device incapable of distinguishing between changes in received light intensity caused by variations in light absorption by the component being monitored (eg oxygen in the blood), and changes in received light intensity caused by variations in the light pathlength due to movement of the subject. The problem is common to all optical monitoring devices and can render these devices inoperative for long periods of time. The problem is particularly severe in critical health care applications, were continuous monitoring is essential.

The device described in WO 94/03102 attempts to address the problem of the motion artefact in measuring $SaO_2$ by using an additional wavelength to enable the motion artefact to be cancelled. Although WO 94/03102 broadly describes the use of a plurality of wavelengths (including the n+1 motion artefact wavelength) the device exemplified uses three wavelengths, namely, a pulse rate wavelength, an $SaO_2$ wavelength and a motion artefact wavelength. However, in practice, the three wavelengths proposed in WO 94/03102 are not sufficient to overcome motion sensitivity.

Generally, medical practitioners desire to measure arterial oxygen saturation ($SaO_2$). For example, conventionally used pulse oximeters measure $SaO_2$. We have now devised an optical measuring or monitoring device which is able to monitor or measure blood oxygen saturation ($SO_2$) and display the arterial blood oxygen saturation non-invasively and to suppress the effects of motion artefact.

Furthermore, existing optical devices do not take into account the variations in transmitted light with varying skin colours. Melanin is present in increasing concentrations from fair through brown to black skin. The peak of its absorption spectrum is at 500 nm decreasing almost linearly with increasing wavelength. Melanin is present in the epidermis, thus, in very high concentrations as is the case in black skin, it can mask the absorption of haemoglobin in the dermis. Even in brown skin, the absorption by melanin is superimposed on that of haemoglobin so that any algorithm which uses the shape of the absorption spectrum in order to produce $SO_2$ value needs to compensate for this fact.

SUMMARY OF THE INVENTION

Thus, we have also devised an optical measuring or monitoring device which is capable of compensating for variations in melanin levels in the skin.

In accordance with this invention, there is provided a sensor device which comprises light source means for emitting a light beam, photodetector means for receiving the light beam after passing through or being reflected within living tissue and arranged to provide signals corresponding to the intensities of the respective wavelength of light received by the photodetector means characterised in that the sensor device measures blood oxygen saturation.

The sensor of the invention may use a spectral wavelength of from 526 to 586 nm.

In a preferred embodiment of the invention the light beam will emit a plurality of wavelengths, the arrangement being such that the signal levels corresponding to the different wavelengths bear a predetermined relationship with each other. A particular advantage of the sensor of the invention is that it only enables a user to compare "slopes" on a graph and the use of a range of different wavelengths allows for a more accurate determination without an increase in costs. In a preferred embodiment of the invention 3 or more different wavelengths are used, the optimum number of wavelengths is 5 or 6 and preferably 6.

It is also an important feature of the present invention that at least one or more of the wavelengths used are isobestic wavelengths. For the sake of clarity, by the term isobestic wavelength we mean a wavelength at which oxygenated haemoglobin and deoxygenated haemoglobin absorb the same amount of light. In a preferred embodiment substantially most of the wavelengths used are isobestic wavelengths. When six wavelengths are used it is preferred that five of them are isobestic wavelengths. In this preferred embodiment the sixth wavelength is one at which there is maximum difference between the absorption of light of oxygenated haemoglobin and deoxygenated haemoglobin.

Generally the device and technique of the present invention measures oxygen saturation ($SO_2$) ie the value of oxygen saturation in venous and arterial tissue combined. Because oxygen saturation in venous tissue is usually low it is well known that the value of $SO_2$ is less than that of $SaO_2$. In the technique of the invention we call the difference the scaling factor $\Delta$, such that $$SaO_2 - SO_2 = \Delta$$

Thus the technique of the invention initially measures $SaO_2$ using a conventional arterial blood oxygen meter eg a pulse oximeter. $SO_2$ is then measured to determine and thus subsequently $SO_2$ measurements made using the device of the invention are, corrected by the value of $\Delta$. Furthermore, the device and technique of the invention continually, although intermittently, allows $SaO_2$ and thereby $\Delta$ to be checked.

The sensor device of the invention is generally an optical measuring or monitoring device.

The sensor may be attached to the chest or abdomen of an infant. The tip of the sensor may incorporate a mirror and is provided with an optical fibre light transmitting cable such that the fibre cable lies flat on the surface of the skin. White light (20 to 50 W quartz halogen light bulb) is preferred and is transmitted along an optical fibre to the skin where multiple scattering occurs as photons interact with cellular and subcellular particles. Light can be absorbed by the haemoglobin present in the blood flowing in the tissue below the sensor before being scattered back along receiving optical fibres. The scattered light can be transmitted along a plurality eg in the preferred embodiment 6 separate fibres to 6 photodetectors via narrow-band optical filters all in the range 500 to 600 nm (green/yellow visible light) and especially between 526 and 586. Generally, the number of detectors should be the same as the number of transmitting fibres. The sensor may optionally be heated above normal body temperature, to eg 40° C. and up to 42° C. for short periods the temperature may even reach 44° C. Alternatively, a single fibre of from 50 to 150 nm in diameter may be used with one to three white LEDs.

Although the sensor of the invention may be adapted to operate with either transmitted light or reflected light, it is preferred that it operates on reflectance (remittance). Thus in contrast to, eg a pulse oximeter the transmitters and the sensors are situated on the same side of the tissue when in use.

According to a further feature of the invention we provide a "hand held" sensor device as hereinbefore described.

In particular, in the "hand held" sensor of the invention the optical fibre transmitting cable(s) may be replaced by a light emitting diode (LED) which significantly reduces the complexity of the sensor.

Before use, the sensor is normalised against darkness and a standard white surface, and the signal from each photodiode is measured to obtain the overall dark and "white balance" figures. Signal processing includes averaging for a period between 10 milliseconds to 10 seconds, subtracting the white balance signal, and taking a logarithm to produce a transmittance at each wavelength.

In the preferred embodiments, the use of 6 wavelengths gives the technique a considerable advantage over the pulse oximetry method which uses the minimum number of wavelengths necessary to obtain the information required. The use of more wavelengths in our method gives the technique stability against spurious disturbances at a particular wavelength, enables flexibility in the algorithm to cope with factors such as skin colour. Nevertheless, the sensor of the invention can utilise either oximetry or pulsed oximetry.

Averaging of the signal over a second or more also removes motion artefacts. It is also the case that the technique operates in the visible wavelength range. Thus, although the penetration of light into tissue is much less, the influence of poor contact with the tissue may also be considerably less thus reducing movement artefact. It is important to emphasis that our technique does not measure pulsatility as in the case in pulse oximetry.

$SO_2$ is the ratio of the oxyhaemoglobin concentration [$HbO_2$] to the total concentration of haemoglobin ([$HbO_2$]+[Hb], where [Hb] is haemoglobin concentration) expressed as a percentage.

$$SO_2 = \frac{[HbO_2] \times 100}{[HbO_2] + [Hb]}$$

$SaO_2$ is arterial oxygen saturation.

The reflected absorptions (A) at six wavelengths (500, 528, 550, 560, 572 and 586 nm) are used to calculate two parameters HbI and OXI:

$$HbI = |A_{528} - A_{500}|/28 + |A_{550} - A_{528}|/22 + |A_{572} - A_{550}|/22 + |A_{586} - A_{572}|/14$$

$$OXI = (|A_{560} - A_{550}|/10 + |A_{572} - A_{560}|/12) HbI$$

$SO_2$ is calculated from the formula:

$$SO_2 = 100 * (OXI - OXI_0)/(OXI_{100} - OXI_0)$$

Where $OXI_0$ and $OXI_{100}$ are empirically determined values for OXI at $SO_2$ values of 0% and 100% in skin. HbI is the haemoglobin index such that $$HbI \times k = [Hb]$$

where k is a constant.

The spectral range used for the algorithm is from 526 to 586 nm and 22 absorption values are recorded within that range. The first process is to carry out a Kubelka and Monk transformation which reduces the intrinsic effect of the scattering of light within the skin.

The following operation is carried out:

$$\text{K-B Transformed spectrum} = 0.5 \times (R^2)/(1-R)$$

where R is the remitted spectrum (Reference: Kubelka, P and Munk F, Ein eitrag zur Optik der Farbanstriche, Zeitschrift fur technische Physik, 11a:593–601 (1931)).

In a paper presented by Wolfgang Dümmler in 1988, he describes that, according to the Kubelka-Munk theory (see Section II.2), the remission of an infinitely thick sample is dependent only on the quotients of absorption and scattering coefficients and is given by:

$$R_\infty = A/S + 1 - \sqrt{\{A/S(A/S+2)\}}$$

The equation can be solved explicitly according to A/S $$A/S = 0.5(R_\infty + 1/R_\infty) - 1$$

where R is the remitted spectrum that is the spectrum of light scattered back from the skin.

The transformed spectra are then "straightened" by subtracting the interpolated straight line joining the absorption values at the isosbestic wavelengths of 526 and 586 nm. This, in part compensates for the melanin concentration.

The straightened spectra are normalised by division by the integral of the absorption values from 526 to 586 nm.

The algorithm can make use of two reference spectra. These spectra may be from whole blood (measured in a cuvette) or spectra recorded in skin or the mean spectra recorded from several individuals. One reference spectrum is of fully oxygenated haemoglobin the other is of fully deoxygenated haemoglobin. The fully oxygenated spectrum is obtained by equilibration of whole blood in the cuvette with 95% oxygen and 5% $CO_2$ at 37° C. or, in skin of the forefinger heated to 44° C. at maximal reactive hyperaemia following release of the inflatable cuff after 6 minutes of brachial artery occlusion. The fully deoxygenated spectrum is obtained by equilibration of whole blood in the cuvette with 95% $N_2$ and 5% $CO_2$ at 37° C. or, in skin of the forefinger heated to 44° C. at the end of a 6 minute period of brachial artery occlusion prior to release of the inflatable cuff. The reference spectra are K-M transformed, "straightened" and normalised as described above.

An iterative process sequentially "mixes" the two reference spectra in increments of 1% until the best least squares fit is achieved with the measured spectrum using all the absorption values at the 22 wavelengths. The iteration typically starts by adding 100 parts of the fully oxygenated spectrum to 0 parts of the fully deoxygenated spectrum, then 99 parts of the fully oxygenated spectrum to 1 part of the fully deoxygenated spectrum and so forth until the sum of the squares of the differences between the measured absorption values and those obtained by combining the reference spectra reaches its minimum value. The resultant $SO_2$ value is the proportion of the oxygenated reference spectrum in the best fitted spectrum (eg 80 parts of the fully oxygenated spectrum with 20 parts of the fully deoxygenated spectrum would give an $SO_2$ value of 80%).

A maximum limit on the least squares value is stipulated such that noise or artefacts in the recorded spectra lead to the rejection of the $SO_2$ value.

A further important aspect of this invention is the fact that our technique measures arterial blood oxygen saturation. This is achieved in the following way: at normal skin temperature an optical measurement made on the skin of a patient would measure the oxygen saturation of a mixture of venous and arterial blood in the capillaries. In our technique we heat the skin below the sensor to below 40° C. The effect of this application of heat is to cause an increase in skin blood flow, sufficient to cause the oxygen saturation of the blood in the capillaries in the skin to equilibrate with the arterial blood supply. In this way the optical device will measure the equivalent of arterial blood oxygen saturation.

According to a further feature of the invention we provide a method of monitoring of SIDS in infants which comprises attaching a calibrated sensor as hereinbefore described to the skin of a patient and emitting white light, detecting and a measuring the scattered light.

According to a further feature of the invention we provide a sensor device which measures $SO_2$ as hereinbefore described coupled to an oximeter eg a pulse oximeter, which is conventionally known per. The sensor device of this embodiment will measure $SO_2$, while the pulse oximeter will measure $SaO_2$, at least intermittently, and allowing the scaling factor $\Delta$ to be calculated and intermittently monitored. Thus the sensor device of this embodiment measures $SO_2$ but displays $SaO_2$.

Thus according to a yet further feature of the invention we provide a method of $SaO_2$ monitoring which comprises measuring $SO_2$ and adding a scaling factor $\Delta$ as hereinbefore defined.

The method of the invention preferentially comprises the use of a sensor device of the invention. In the most preferred method, the sensor is used to continually measure $SO_2$ and to intermittently measure $SaO_2$ allowing the motion artefact to be annulled.

In a further embodiment, the method of the invention as hereinbefore described includes the use of the Kubelka and Monk transformation to account for melanin levels in skin.

BRIEF DESCRIPTION OF THE DRAWING FIGS.

The invention will now be described by way of example only and with reference to the accompanying drawings in which FIG. 1 is a schematic representation of the optical measurement method of the invention;

FIGS. 2(a) and 2(b) are both graphs which illustrate how the $SO_2$ values are calculated;

Figure 1:
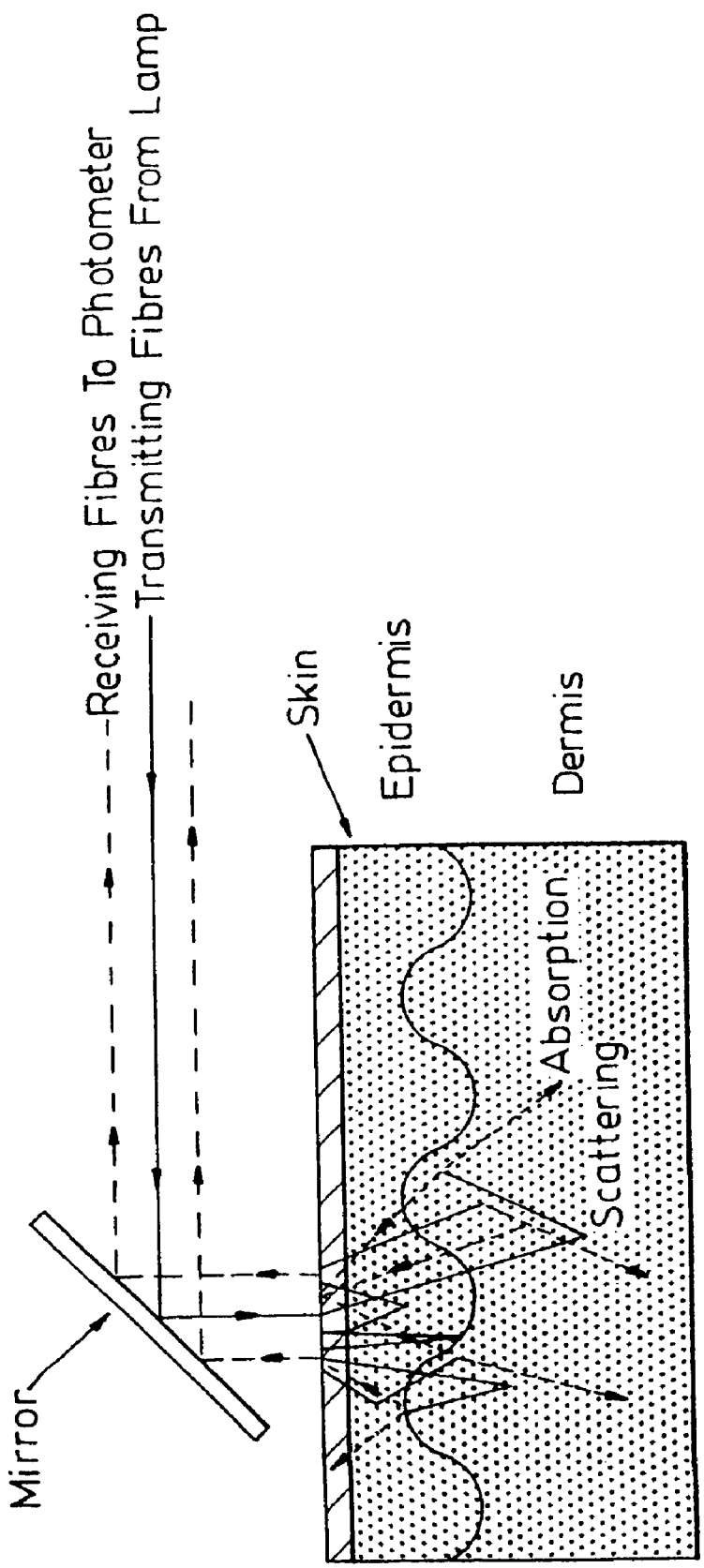

FIG. 6a to d are graphs representing measured $SO_2$ values for different skin colours.

DETAILED DESCRIPTION OF THE DRAWING FIGURES

And Experimental Data and Preferred Embodiments

With reference to FIG. 1, an optical blood saturation sensor (1) comprises transmitting fibres (2) from a lamp (not shown) which transmit light to be reflected from a mirror (3) onto the skin (4) of a patient where the light in proportions is absorbed and scattered or reflected depending upon the oxygen content of the haemoglobin and the wavelengths of light used. Reflected light (5) is detected by receiving fibres (6) and transmitted to a photometer (not shown).

Figure 2A:
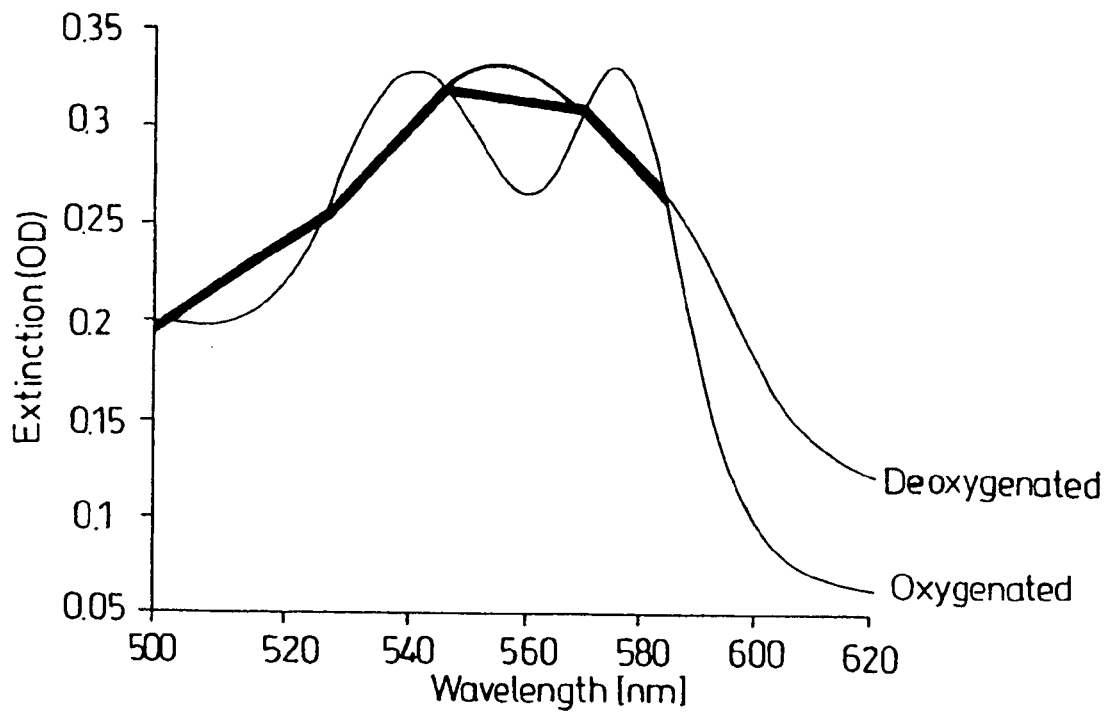
Figure 2B:
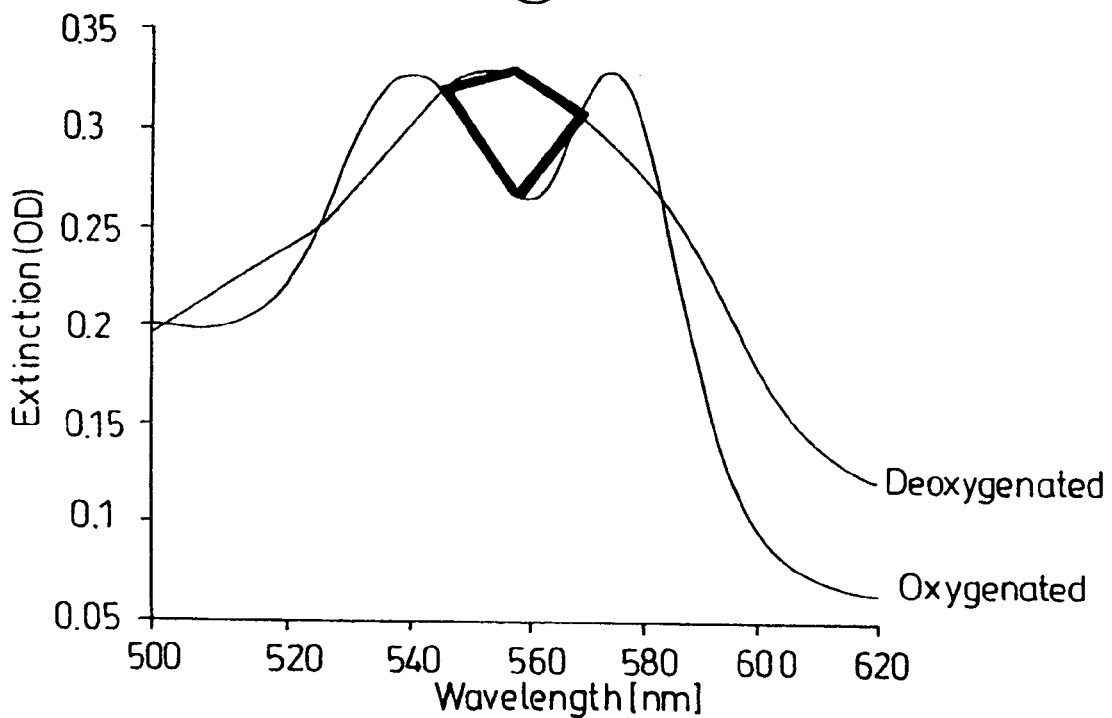

The measurement technique can best be understood by reference to FIGS. 2(a) and 2(b). Analysis of the data to obtain an index of haemoglobin concentration and arterial oxygen saturation ($SaO_2$) is carried out as follows: the gradients between 5 isobestic wavelengths (500, 520, 548, 575 and 586 nm) are added to given an index which is related to the haemoglobin concentration. This index is used to normalise the measured tissue spectra. The oxygen saturation ($SO_2$) is calculated from the gradients between the absorption peaks for de-oxygenated haemoglobin (560 nm) and the two adjacent isobestic wavelengths (548 and 575 nm) of the normalised spectra.

The most important factor influencing the stability of the $SaO_2$ lies in our 6 wavelength analysis technique which incorporates the 5 isobestic wavelengths and the single oxygenated/deoxygenated peak. The two accompanying Figures illustrate how the HbI and $SO_2$ values are obtained from the spectra. HbI is the sum of the moduli of the slopes of the lines connecting the isobestic points as shown in the first FIG. 2(a): it can be seen that any change in the general level of the signal, such as may occur due to small changes in the distance of the probe from the skin would not have any significant influence on this value. The absorption spectrum may shift up or down, but the sum of the moduli of the slopes remains constant.

$SO_2$ values (FIG. 2(b)) are calculated from the sum of the moduli of the slopes of the extinction values between the neighbouring isobestic points and the deoxygenated peak, normalised to the HbI value. We thus obtain not only an $SO_2$ value but, on the way, we can also obtain a measure of relative haemoglobin concentration (HbI) from our measurements.

Figure 3:
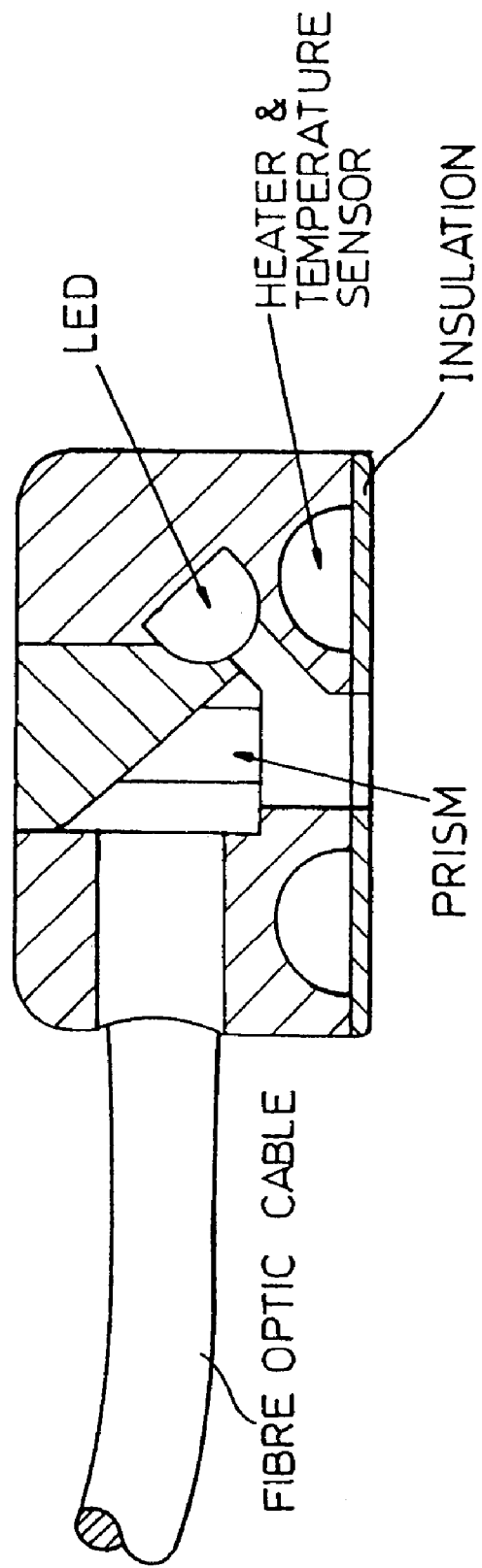
FIG. 3 is a "hand held" sensor according to the invention.

With reference to FIG. 3 a hand held sensor (7) may comprise a fibre optic cable (8), a prism (9), an LED (10) and a heater and temperature sensor (11). The sensor (7) is provided with insulation (12).

Figure 4:
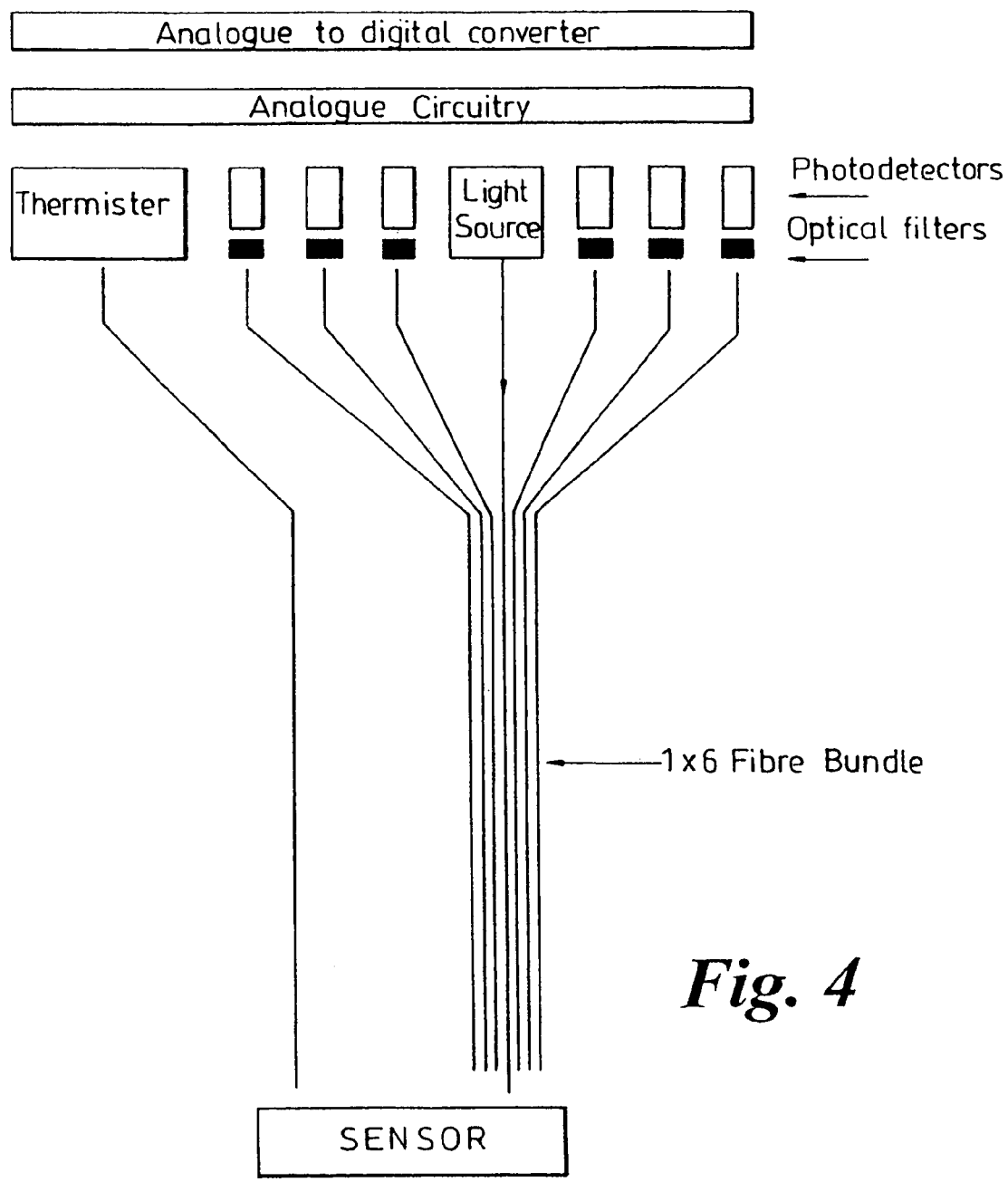
FIG. 4 is a representation of the schematic layout of the optical system of the sensor of the invention.
Figure 5:
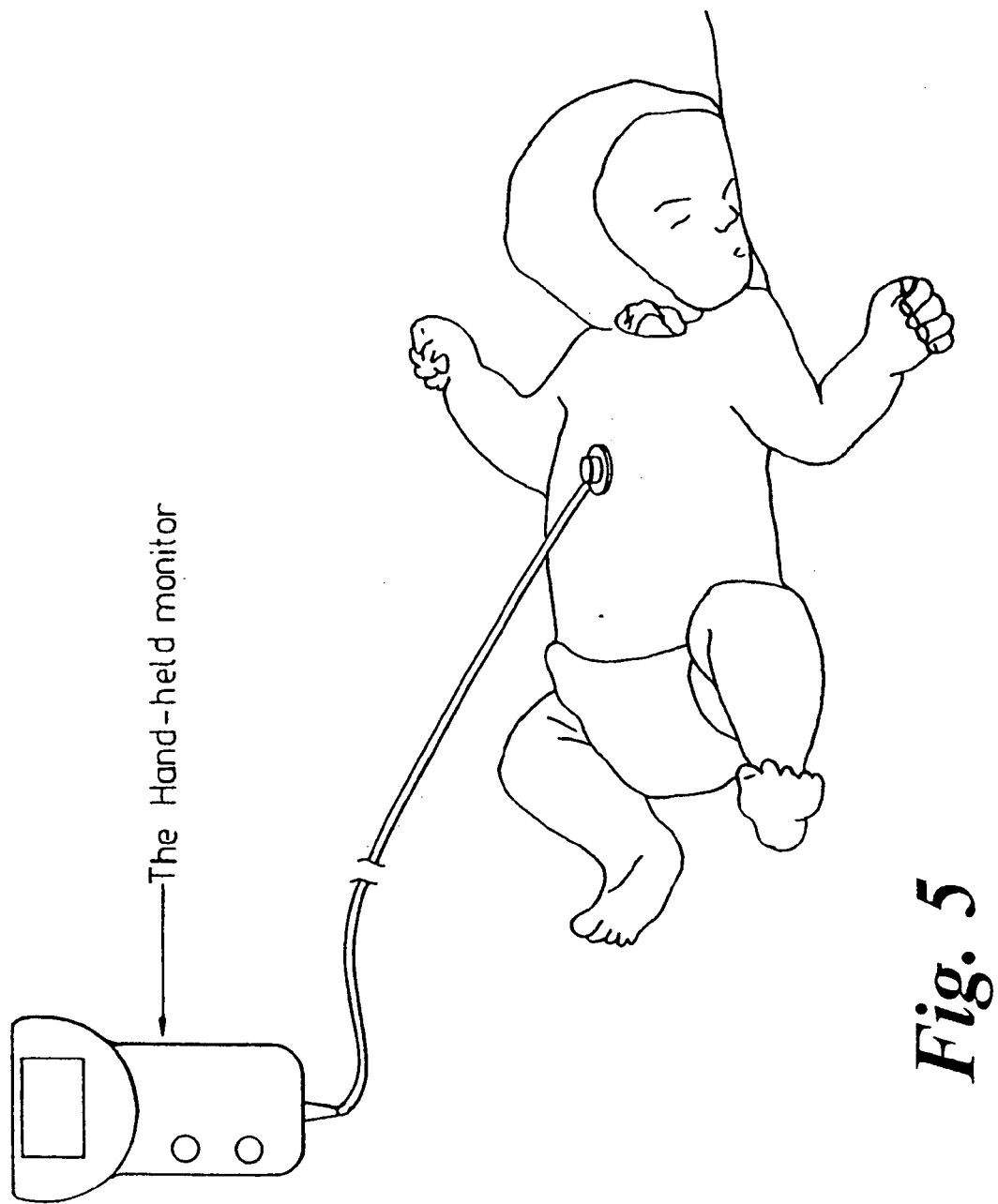
FIG. 5 is a representation of the hand held sensor of the invention in use.
Figure 6A:
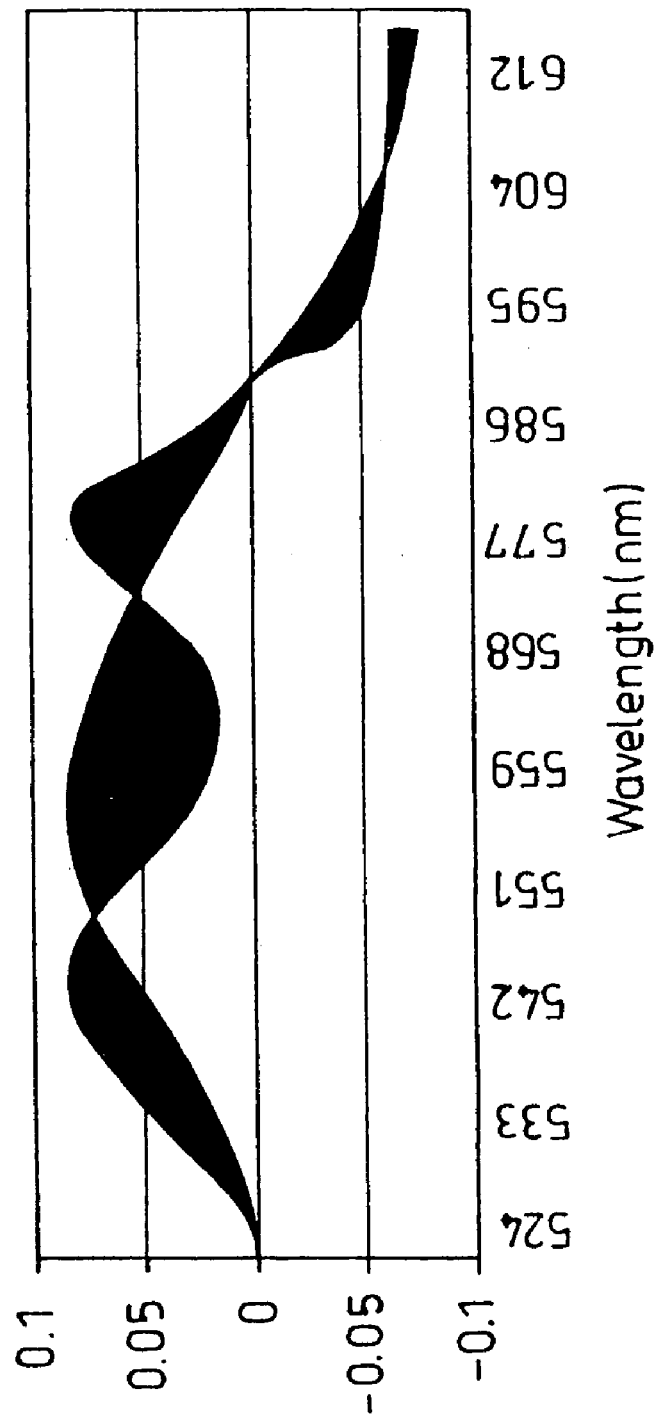
Figure 6B:
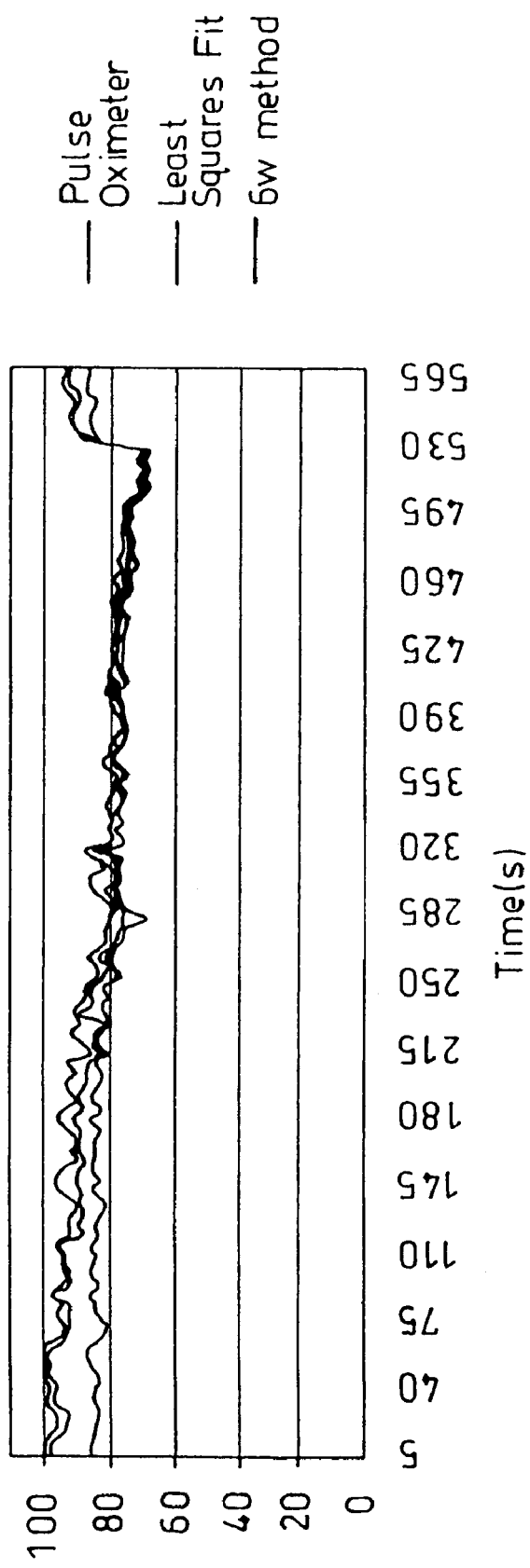
Figure 6C:
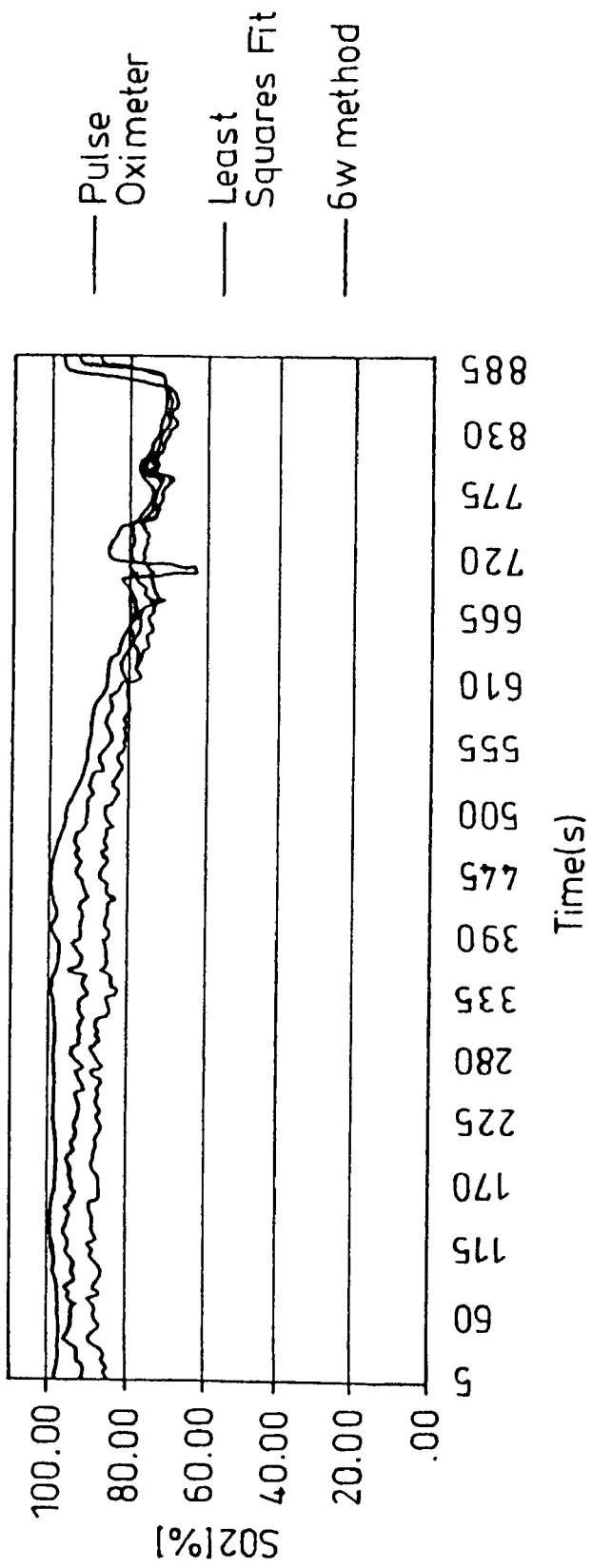
Figure 6D:
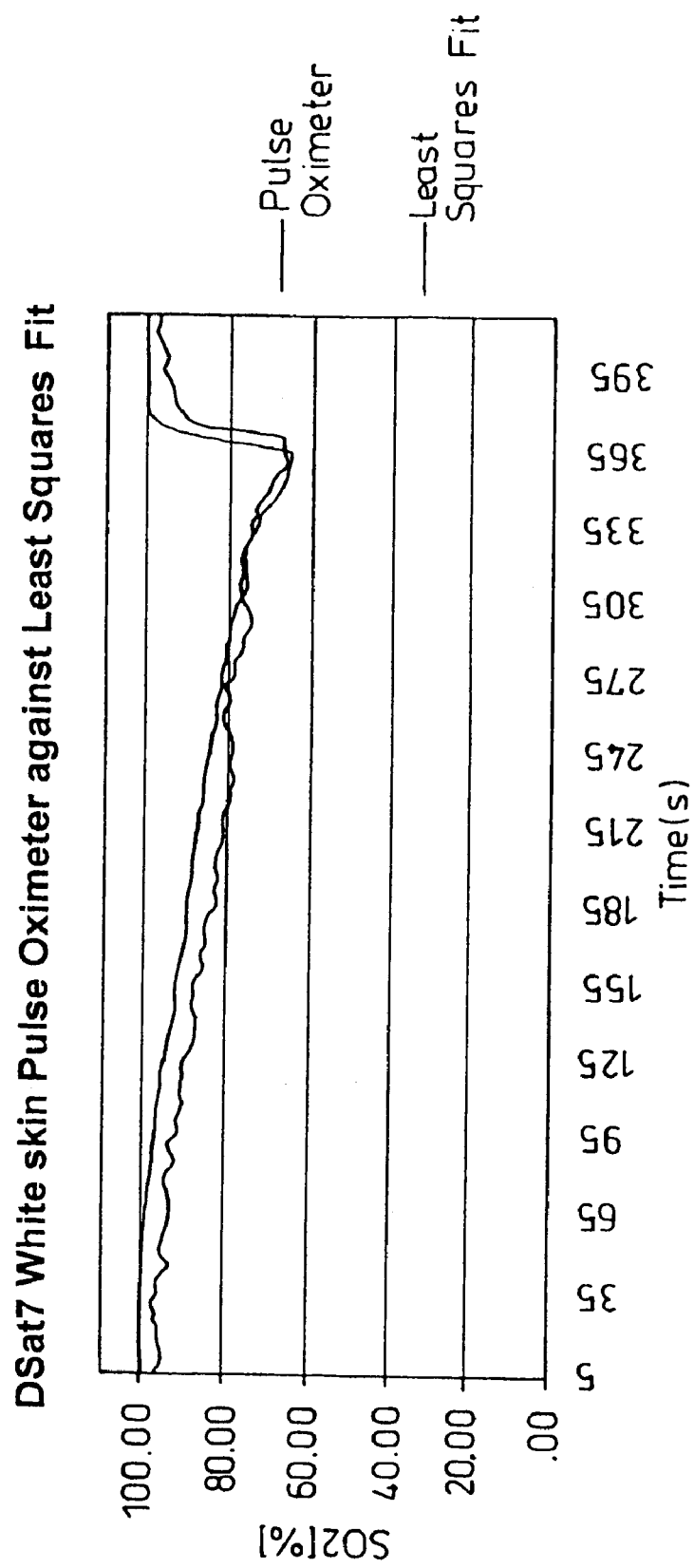

With reference to FIG. 4, a sensor (13) is provided with 6 fibre bundles (14), a light source (15) and a thermistor (16).

The invention claimed is:

1. A method for $SO_2$ monitoring, comprising the steps of:
calculating an estimate of $SO_2$ in blood to be monitored;
correcting said estimate of $SO_2$ in blood by a scaling factor;
transmitting light containing a plurality of wavelengths into the blood;
measuring a remitted spectrum over the plurality of wavelengths;
calculating a measured blood absorption spectrum from the remitted spectrum;

estimating local rates of change in the measured blood absorption spectrum at a plurality of the wavelengths, including at least one isobestic wavelength; and, calculating the estimate of $SO_2$ as a function of absolute values of the local rates of change of the measured blood absorption spectrum.

2. The method for $SO_2$ monitoring according to claim 1, wherein before said step of calculating the estimate of $SO_2$, further comprising the steps of:

removing effects of light scattering from the measured blood absorption spectrum;

calculating an area under the measured blood absorption spectrum after said step of removing effects of light scattering; and, normalizing the measured blood absorption spectrum by the area under the measured blood absorption spectrum determined during said step of calculating.

3. The method for $SO_2$ monitoring according to claim 1, further comprising the step of applying a Kubelka Monk transformation to the measured blood absorption spectrum.

4. The method for $SO_2$ monitoring according to claim 1, wherein the step of calculating the estimate of $SO_2$ comprises the steps of:

computing a hemoglobin index value as a function of absolute values of the local rates of change of the measured blood absorption spectrum between a plurality of pairs of isobestic points, whereby the hemoglobin index value is independent of blood oxygenation;

computing an oxygenation parameter as a function of absolute values of the local rates of change of the measured blood absorption spectrum between a plurality of isobestic points and at least one non-isobestic point, whereby the oxygenation parameter is dependent on blood oxygenation;

normalizing the oxygenation parameter by the hemoglobin index value; and, estimating $SO_2$ as a measure of the level of the normalized oxygenation parameter relative to a predetermined fully deoxygenated reference value and a fully oxygenated reference value.

* * * * *